United States Patent [19]
Bond

[11] 3,978,872
[45] Sept. 7, 1976

[54] TOOTHPICK

[76] Inventor: Jesse H. Bond, 1038 Shephard, Corpus Christi, Tex. 78412

[22] Filed: Mar. 12, 1975

[21] Appl. No.: 557,819

[52] U.S. Cl. ................................................. 132/89
[51] Int. Cl.² ......................................... A61C 15/00
[58] Field of Search ........................ 132/89, 90, 91

[56] References Cited
UNITED STATES PATENTS

| | | | |
|---|---|---|---|
| 1,355,037 | 10/1920 | Dziuk | 132/90 |
| 1,997,877 | 4/1935 | Spanel | 132/89 |
| 2,931,370 | 4/1960 | Jackson | 132/89 |
| 3,563,253 | 2/1971 | Barman | 132/89 |

*Primary Examiner*—G.E. McNeill
*Attorney, Agent, or Firm*—G. Turner Moller

[57] ABSTRACT

There is disclosed a toothpick in which one end thereof is provided with a pair of hollow-ground surfaces terminating in a thin bladed end. The bladed end is sufficiently thin to pass between adjacent teeth in the mouth of the user.

16 Claims, 4 Drawing Figures

TOOTHPICK

There are two types of toothpicks presently on the market. The first type provides a generally cylindrical central portion and tapered pointed ends. the second type is generally flat and tapers gradually from one wide end to a narrower end. Probably the most aggravating occurrence to toothpick users is the inability to dislodge a food particle from between the teeth. With toothpicks of the type that are presently on the market, the primary difficulty is that the ends are not sufficiently thin to extend fully between the teeth.

In this invention, the toothpick end is provided with a pair of hollow-ground surfaces terminating in a bladed end sufficiently thin to pass fully between adjacent teeth in the mouth of the user. The hollow-ground shape provides a substantial length of the bladed end that is quite thin and yet provides surprising strength.

The prior art is replete with toothpicks of various shapes for various purposes. Among those which exhibit arcuately converging surfaces terminating in an end are found in U.S. Pat. Nos. 1,581,501; 1,624,054; 2,925,087; 3,050,072 and 3,779,256. Each of these prior art devices has one or more disadvantages among which are that the bladed end is insufficiently thin to extend fully between adjacent teeth and the mouth of the user, that the device is of intricate construction requiring a multiplicity of manufacturing operations, that the bladed end formed by the converging surfaces is inappropriately related to the handle and other disadvantages as will become more fully apparent as this description proceeds.

In summary, one aspect of this invention comprises a unipartite toothpick comprising an elongate element providing a handle portion having a longitudinal axis, one end of the element being provided with a pair of surfaces arcuately converging relative to a pair of parallel axes toward the longitudinal axis and terminating in a bladed end sufficiently thin to extend between human teeth throughout a distance from the front thereof to the rear thereof.

In summary, another aspect of this invention comprises a method of manufacturing toothpicks comprising placing an end of an abradable member in the nip between a pair of rotating abrading elements.

IN THE DRAWINGS

Figure 1:
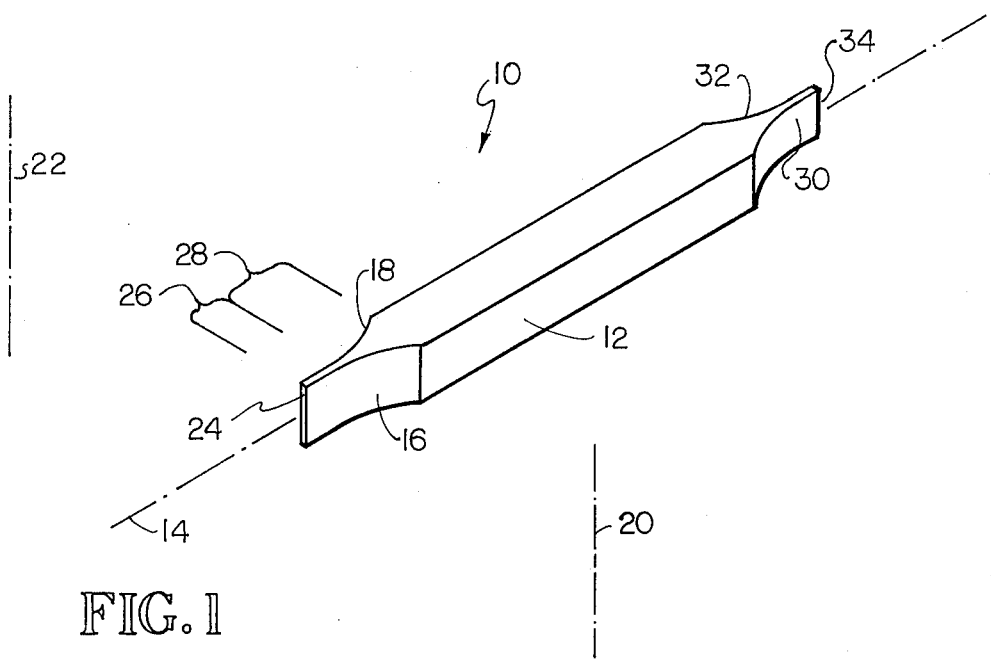
FIG. 1 is an isometric view of a toothpick made in accordance with this invention.

Referring to FIG. 1, there is illustrated a first embodiment of a toothpick 10 comprising an elongate element 12 which is illustrated as being of generally square cross-section but which may be of any suitable cross-sectional shape. The elongate element 12 provides a handle portion defining a longitudinal axis 14. One end of the element 12 is provided with a pair of surfaces 16, 18 which arcuately converge relative to a pair of parallel axes 20, 22 toward the longitudinal axis 14. The surfaces 16, 18 terminate in a bladed end 24 sufficiently thin to extend fully between human teeth, i.e. throughout a distance from the front thereof to the rear thereof. The surfaces 16, 18 are conveniently of hollow-ground shape in which the trace of the surface 16, for example, is defined by an arc of constant radius taken from the axis 20. The surfaces 16, 18 are conveniently mirror images. It will also be seen that the bladed end 24 is not pointed and therefore is not apt to puncture cloth, for example a shirt pocket.

Because of the arcuately converging relationship between the surfaces 16, 18 the bladed end 24 defined therebetween tapers very gradually through an end portion 26 and tapers more abruptly through an end portion 28. It is highly advantageous that the thickness of the bladed end 24 at the junction of the end portions 26, 28 be quite thin and sized to pass between human teeth. In this circumstance, the end portion 26 becomes the operative element of the toothpick 10.

The opposite end of the toothpick 10 may be provided with surfaces 30, 32 arcuately converging toward the axis 14 to define a bladed end 34 therebetween in much the same manner that the surfaces 16, 18 converge. In the illustration of FIG. 1, it will be apparent that the bladed ends 24, 34 are parallel although they may be disposed differently, for example at right angles, if desired.

Figure 2:
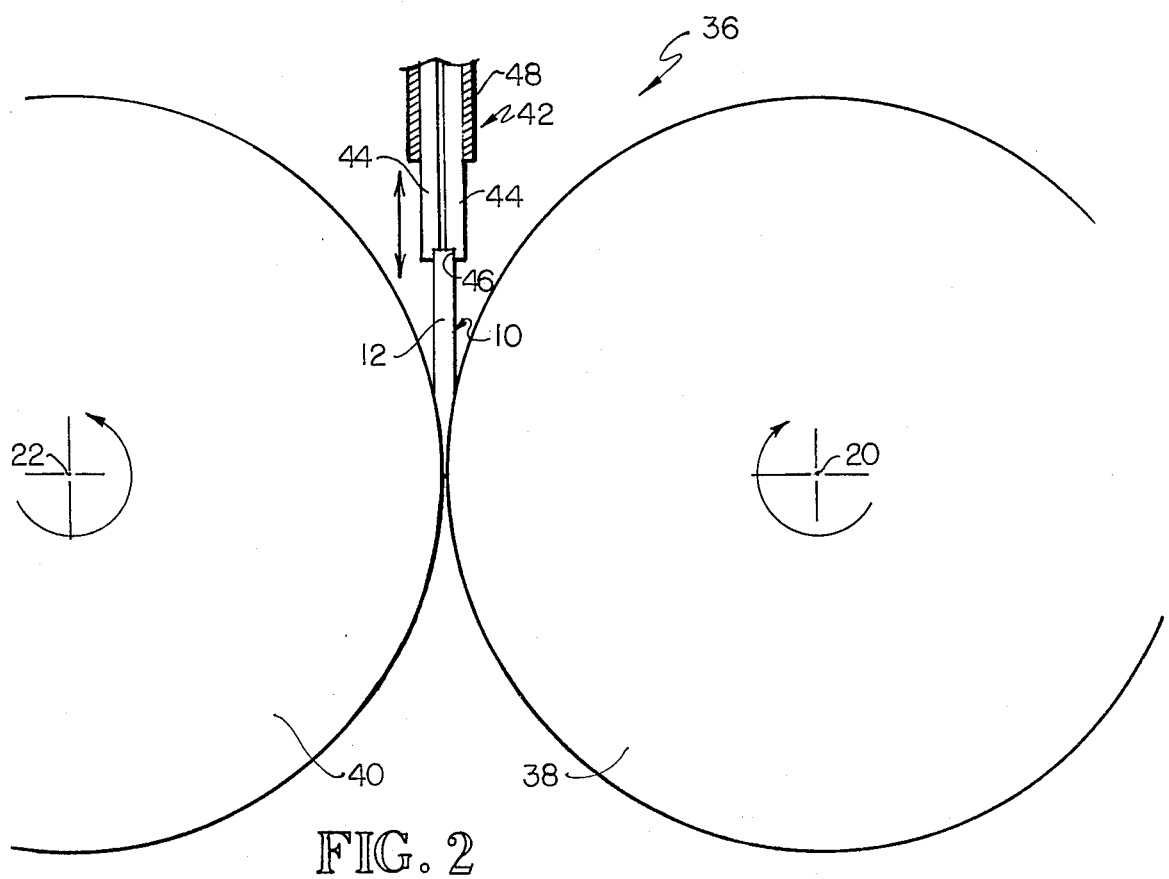
FIG. 2 is a view of apparatus utilized in the manufacture of the toothpick of FIG. 1.

Referring to FIG. 2, there is illustrated an apparatus 36 for manufacturing the toothpick 10 comprising a pair of grinding wheels 38, 40 disposed for rotation about respective parallel axes 20, 22, the placement of which determine the curvature of the surfaces 16, 18. The apparatus 36 also comprises means 42 for holding the element 12 and may comprise a plurality of spring fingers 44 which define a recess 46 for receiving the end of the element 12 and a reciprocable collar or sleeve 48 which may be advanced toward the element 12 for biasing the spring fingers 44 into grasping relation with the end of the element 12.

In use, the element 12 is positioned in the recess 46 and the collar 48 advanced to close the fingers 44 around the end of the element 12. The holding means 42 is then advanced linearly toward the nip between the grinding wheels 38, 40, to abrade the end of the element 12 in accordance with the shape defined by the circumferences of the wheels 38, 40.

In this regard, it will be apparent that the size of the elongate element 12, the diameters of the wheels 38, 40, and the placement of the axes 20, 22 control the shape of the surfaces 16, 18. The element 12 is conveniently of approximately the same width as conventional wooden matches, i.e. 0.10–0.15 inches square. It will be apparent that if the grinding wheels 38, 40 are relatively small, the surfaces 16, 18 will rapidly converge toward the bladed end 24. At some minimum size of the grinding wheels 38, 40, the end portions 26, 28 are not sufficiently thin along a substantial distance to extend fully between adjacent teeth in the mouth of the user. It is presently believed that the minimum diameter of the grinding wheels 38, 40 is on the order of about three inches. It will also be appreciated that as the grinding wheels 38, 40 become larger, the tapered end portions 26, 28 of the element 12 become unduly long resulting in decreased strength in the outer end portion thereof and requiring excessive abrasion. It is presently believed that the maximum diameter of the grinding wheels 38, 40 should be on the order of about eight inches. The optimum diameter of the grinding wheels 38, 40 is in the range of 4–6 inches. The wheels 38, 40 should be placed such that the bladed end 24 is quite thin, e.g. on the order of 0.01–0.02 inches in thickness.

Figure 3:
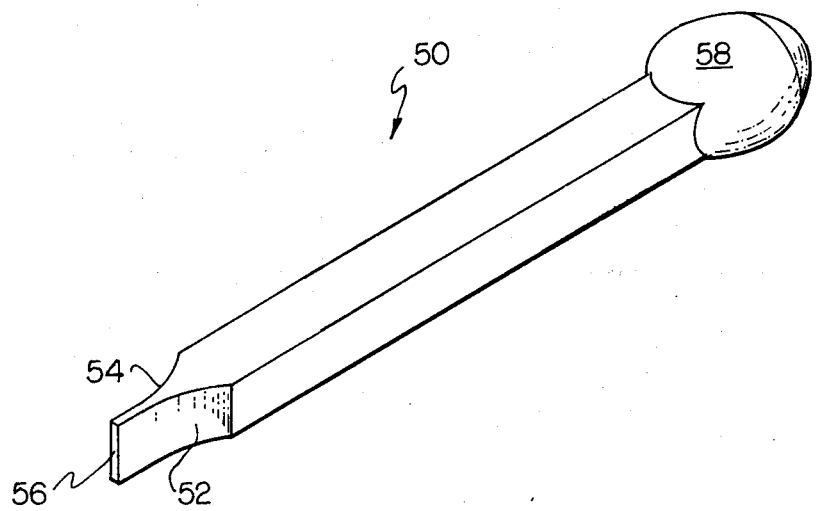
FIGS. 3 and 4 comprise isometric views of other embodiments of this invention.

Referring to FIG. 3, there is illustrated another embodiment of a toothpick 50 of this invention providing hollow-ground surfaces 52, 54 at one end thereof terminating in a thin bladed end 56 and a match head 58 at the other end thereof.

Figure 4:
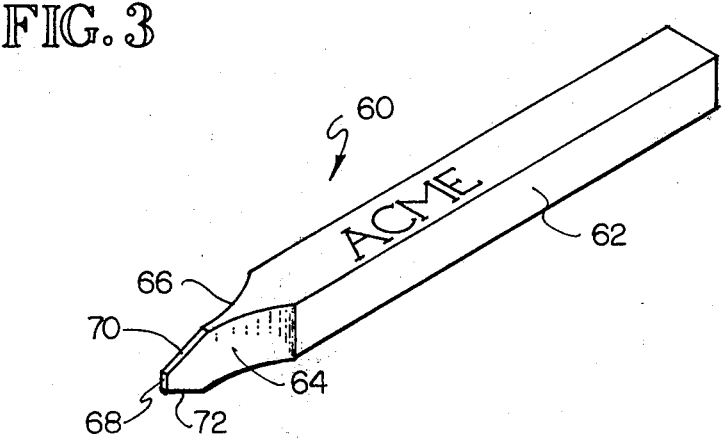

Referring to FIG. 4, there is illustrated another embodiment of a toothpick 60 in accordance with this invention providing a handle element 62 and a pair of hollow-ground surfaces 64, 66. Rather than the surfaces 64, 66 terminating in a bladed end 68 of the same thickness of the element 62, a secondary shaping operation hs been performed to provide a pair of surfaces 70, 72 converging toward the end 68 in traces transverse to the surfaces 64, 66. It will accordingly be seen that the bladed end 68 is of minor extent when compared to the bladed ends 24, 56 of the embodiments of the FIGS. 1 and 3. The surfaces 70, 72 may be planar, as illustrated, or of hollow-ground shape.

As shown in FIG. 4, a suitable advertising message may be imprinted on the handle portion 62.

The toothpicks 10, 50, 60 are importantly unipartite, by which is meant that they are of one piece of material without joints or connections with other pieces of material. When of an abradable material, such as wood or plastic, the toothpicks 10, 50, 60 can be quickly and inexpensively manufactured in accordance with the technique of FIG. 2. It will be equally apparent that the toothpicks 10, 50, 60 may be cast or molded from organic plastic materials into a unipartite structure.

I claim:

1. A unipartite toothpick comprising an elongate element of an abradable material providing a handle portion having a longitudinal axis, one end of the element being provided with a pair of arcuately converging surfaces of hollow-ground shape, each surface defining a radius about an axis, the last mentioned axes being on opposite sides of the longitudinal axis and being spaced apart a distance in the range of 3–8 inches, the element terminating in a bladed end sufficiently thin to extend between human teeth throughout a distance from the front thereof to the rear thereof.

2. The toothpick of claim 1 wherein the bladed end is of the same width as the element.

3. The toothpick of claim wherein the bladed end is of lesser width than the element.

4. The toothpick of claim 1 wherein the element is of substantially uniform width and substantially uniform thickness, the end surfaces converging from the width dimension to the thin bladed end.

5. The toothpick of claim 1 wherein the opposite end of the element is formed with surfaces arcuately converging toward the longitudinal axis and terminating in a thin bladed end.

6. The toothpick of claim 1 wherein the opposite end of the element is formed with a disparate element.

7. The toothpick of claim 1 wherein the element is wood and the bladed end is unitary with the remainder of the element.

8. The toothpick of claim 1 wherein the element is of organic resin and the bladed end is unitary with the remainder of the element.

9. The toothpick of claim 1 wherein the surfaces are mirror-images.

10. The toothpick of claim 1 wherein the axes are spaced apart a distance in the range of 3–8 inches.

11. The toothpick of claim 1 wherein the axes are spaced apart a distance in the range of 4–6 inches.

12. The toothpick of claim 4 wherein the element width and thickness are substantially the same.

13. The toothpick of claim 5 wherein the opposite bladed ends are parallel.

14. The toothpick of claim 6 wherein the disparate element is a match head.

15. The method of manufacturng a unipartite toothpick from an abradable stock comprising moving the stock into abrading contact with a pair of rotating abrading wheels each having a diameter in the range of 3–8 inches; and abrading the end of the stock into the configuration defined by the nip between the wheels.

16. The method of claim 15 wherein the stock is elongate providing a long dimension and the moving step comprises moving the stock parallel to the long dimension thereof into abrading contact with the abrading wheels.

* * * * *